(12) United States Patent
Robins et al.

(10) Patent No.: US 8,058,311 B2
(45) Date of Patent: Nov. 15, 2011

(54) IMAGING 18F OR 11C-LABELLED ALKYLTHIOPHENYL GUANIDINES

(75) Inventors: Edward George Robins, Singapore (SG); Erik Arstad, London (GB)

(73) Assignee: Hammersmith Imanet Limited, London (GB)

( * ) Notice: Subject to any disclaimer, the term of this patent is extended or adjusted under 35 U.S.C. 154(b) by 891 days.

(21) Appl. No.: 11/917,934

(22) PCT Filed: Jun. 23, 2006

(86) PCT No.: PCT/GB2006/002315
§ 371 (c)(1),
(2), (4) Date: Dec. 18, 2007

(87) PCT Pub. No.: WO2006/136846
PCT Pub. Date: Dec. 28, 2006

(65) Prior Publication Data
US 2010/0143252 A1    Jun. 10, 2010

(30) Foreign Application Priority Data

Jun. 23, 2005 (GB) .................................. 0512770.9

(51) Int. Cl.
A61K 31/155 (2006.01)
A61K 31/405 (2006.01)
A61K 51/00 (2006.01)
(52) U.S. Cl. ....... 514/634; 424/1.11; 564/230; 564/237; 564/238; 564/239
(58) Field of Classification Search ................ 424/1.11, 424/1.37, 1.89, 9.44; 564/238, 634, 239, 564/247, 319, 325
See application file for complete search history.

(56) References Cited

FOREIGN PATENT DOCUMENTS
WO       2004/007440        1/2004
WO    WO-2004/007440    *   1/2004

OTHER PUBLICATIONS

Waterhouse et al, Journal of Labelled Compounds and Radiopharmaceuticals 2002, 45, 955-964.*

Zhao, Robins, et.al., "Synthesis and characterization of N-(2-chloro-5-methylthiophenyl)-N-(3-methylthiopenyl)-N-11Cmethylguanidine 11CCNS 5161, a candidate PET tracer for functional imaging of the NMDA receptors" Journal of Labelled Compounds and Radiopharmaceuticals, vol. 49, Feb. 2006 pp. 163-170.

Waterhouse, et.al., "Synthesis of 11-C N-(2-chloro-5-thiomethylphenyl)-N-methylguanidine (11CGMOM): a candidate PET tracer for imaging the PCP site of the NMDA ion channel" Journal of Labelled Compounds and Radiopharmacueticals vol. 45 2002 pp. 955-964.

Dumont, et.al. "Synthesis and in vitro evaluation of N,N'-diphenyl and N-naphthyl-N'phenylguanidines and N-methyl-D-aspartate receptor ion-channel ligands" Bioorganic and Medicinal Chemistry Letters, vol. 12, 2002, pp. 1583-1586.

Zessin, et.al. "Efficient synthesis of enantiomerically pure thioester precursors of 11CMcN-5652 from racemic McN5652" Journal of Labelled Compounds and Radiopharmaceuticals, vol. 42, 1999 pp. 1301-1312.

Zessin, et.al. "S-18F-Fluoromethyl-(+)-McN5652—A potential PET tracer for imaging the sertoning transporter" Journal of Labelled Compounds and Radiopharmaceuticals, vol. 44, 2001 pp. S196-S197.

Waterhouse, Rikki "Imaging the PCT site of the NMDA ion channel" Nuclear Medicine and Biology Jul. 30, 2003 pp. 869-878.

PCT/GB2006/002315 International Search Report and Written Opinion dated Sep. 2006.

* cited by examiner

*Primary Examiner* — Michael G Hartley
*Assistant Examiner* — Jagadishwar Samala

(57) ABSTRACT

The invention provides a compound of formula (I); or a salt or solvate thereof, wherein: $R^1$ is hydrogen or $C_{1-4}$ alkyl; $R^2$ and $R^4$ are each independently selected from $C_{1-4}$ alkyl, $[^{11}C]C_{1-4}$ alkyl, and $[^{18}F]$—$C_{1-4}$ fluoroalkyl provided that at least one of $R^2$ and $R^4$ is $[^{11}C]C_{1-4}$ alkyl or $[^{18}F]$—$C_{1-4}$ fluoroalkyl; and $R^3$ is halo. Such compounds having use for imaging central nervous system receptors.

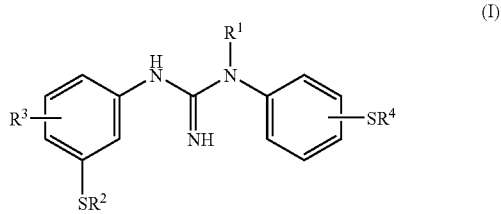

(I)

5 Claims, No Drawings

IMAGING 18F OR 11C-LABELLED ALKYLTHIOPHENYL GUANIDINES

This application is a filing under 35 U.S.C. 371 of international application number PCT/GB2006/002315, filed Jun. 23, 2006, which claims priority to application number 0512770.9 filed Jun. 23, 2005, in Great Britain the entire disclosure of which is hereby incorporated by reference.

The present invention relates to the field of medical imaging, in particular to positron emission tomography (PET) and provides compounds and methods for imaging central nervous system (CNS) receptors.

The N-methyl-D-aspartate (NMDA) receptor is one of the main subtypes of glutamatergic receptors and is widely accepted to play a pivotal role in long term depression, long term potentiation, and developmental neuronal plasticity. NMDA induced excitotoxicity that is due at least partially to over activation or prolonged stimulation of NMDA receptors has been found in many CNS diseases such as stroke, brain or spinal chord trauma, epilepsy, Alzheimer's disease, and Huntington's disease. A number of compounds have been investigated as potential radioligands for studying the NMDA receptor ion-channel site in vivo using PET. However, the majority of these compounds have suffered the disadvantages of poor penetration of the blood brain barrier or high non-specific binding.

WO 94/27591 describes certain substituted guanidines and their use for therapy. WO 2004/007440 describes radiolabelled guanidine derivatives and their use for imaging central nervous system (CNS) receptors, these derivatives have proved to require complicated high performance liquid chromatography (HPLC) purification after synthesis and only provide low to moderate yields with relatively long preparation times of around 45 minutes. Therefore, there exists a need for improved labelling chemistry with respect to overall yields, preparation time and simplicity of purification. Further, to enable longer scanning time and increase the availability of such tracers there is a need for further radioligands for the NMDA receptor.

Accordingly, in one aspect of the present invention, there is provided a compound of formula (I):

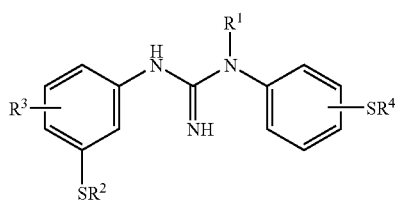

(I)

or a salt or solvate thereof, wherein:
$R^1$ is hydrogen or $C_{1-4}$alkyl;
$R^2$ and $R^4$ are each independently selected from $C_{1-4}$ alkyl, [$^{11}$C]—$C_{1-4}$alkyl, and [$^{18}$F]—$C_{1-4}$ fluoroalkyl provided that at least one of $R^2$ and $R^4$ is [$^{11}$C]—$C_{1-4}$alkyl or [$^{18}$F]—$C_{1-4}$ fluoroalkyl; and
$R^3$ is halo.

$R^1$ is preferably hydrogen or methyl, more preferably methyl.

One of $R^2$ or $R^4$ is preferably —$^{11}$CH$_3$, —$^{11}$CH$_2$CH$_3$, or —$^{11}$CH$_2$CH$_2$CH$_3$, —CH$_2$$^{18}$F, —CH$_2$CH$_2$$^{18}$F, or —CH$_2$CH$_2$CH$_2$$^{18}$F and is more preferably —$^{11}$CH$_3$ or —CH$_2$$^{18}$F; and the other group $R^2$ or $R^4$ is preferably methyl.

$R^3$ is preferably attached to the phenyl ring in the para-position relative to the group —SR$^2$, and in a preferred aspect, $R^3$ is chloro.

The group —SR$^4$ is preferably attached to the phenyl ring in the meta-position relative to the guanidine bridge.

Thus, in a preferred aspect of the invention, there is provided a compound of formula (Ia):

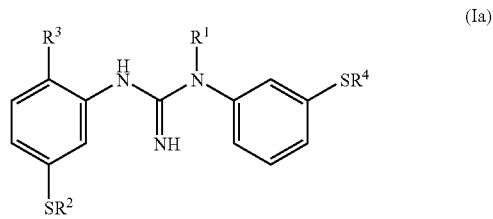

(Ia)

or a salt or solvate thereof, wherein $R^1$, $R^2$, $R^3$, and $R^4$ are as defined for the compounds of formula (I).

Most preferred compounds of formula (I) include:
N-(2-chloro-5-[$^{18}$F]fluoromethylthio)-phenyl-N'-(3-methylthio)-phenyl-N'-methylguanidine;
N-(2-chloro-5-(2-[$^{18}$F]fluoroethylthio))-phenyl-N'-(3-methylthio)-phenyl-N'-methylguanidine;
N-(2-chloro-5-methylthio)-phenyl-N'-(3-[$^{18}$F]fluoromethylthio)-phenyl-N'-methylguanidine;
N-(2-chloro-5-methylthio)-phenyl-N'-(3-(2-[$^{18}$F]fluoroethylthio))-phenyl-N'-methylguanidine;
N-(2-chloro-5-[$^{11}$C]methylthio)-phenyl-N'-(3-methylthio)-phenyl-N'-methylguanidine;
N-(2-chloro-5-methylthio)-phenyl-N'-(3-[$^{11}$C]methylthio)-phenyl-N'-methylguanidine;
N-(2-chloro-5-[$^{11}$C]ethylthio)-phenyl-N'-(3-methylthio)-phenyl-N'-methylguanidine; and
N-(2-chloro-5-methylthio)-phenyl-N'-(3-[$^{11}$C]ethylthio)-phenyl-N'-methylguanidine or a salt or solvate of any thereof.

Suitable salts according to the invention, include physiologically acceptable acid addition salts such as those derived from mineral acids, for example hydrochloric, hydrobromic, phosphoric, metaphosphoric, nitric and sulphuric acids, and those derived from organic acids, for example tartaric, trifluoroacetic, citric, malic, lactic, fumaric, benzoic, glycollic, gluconic, succinic, methanesulphonic, and para-toluenesulphonic acids.

As demonstrated below, the compounds of formula (I) and (Ia) have use as radioligands for the NMDA receptor. Therefore, according to a further aspect of the invention, there is provided a compound of formula (I) or (Ia) as defined above, or a salt or solvate thereof, for use in an in vivo diagnostic or imaging method such as PET. Suitably, a compound of formula (I) or (Ia) as defined above, or a salt or solvate thereof may be used to image the NMDA receptor in healthy human volunteers.

Suitably, the compounds of formula (I) or (Ia) or salt or solvate thereof are useful for in vivo imaging of NMDA receptors and thus have utility in the diagnosis of NMDA-mediated disorders, such as stroke, brain or spinal chord trauma, epilepsy, Alzheimer's disease, or Huntington's disease. Accordingly, there is further provided use of a compound of formula (I) or (Ia) or a salt or solvate thereof in the manufacture of a radiopharmaceutical for the in vivo diagnosis or imaging of an NMDA-mediated disease.

In the alternative, there is provided a method for the in vivo diagnosis or imaging of NMDA-mediated disease in a subject, preferably a human, comprising administration of a compound of formula (I) or (Ia) or a salt or solvate thereof. The method is especially preferred for the in vivo diagnosis or imaging of stroke, brain or spinal chord trauma, epilepsy, Alzheimer's disease, or Huntington's disease.

A compound of formula (I) or (Ia) or a salt thereof is preferably administered in a radiopharmaceutical formulation comprising the compound of the invention and a pharmaceutically acceptable excipient. A "radiopharmaceutical formulation" is defined in the present invention as a formulation comprising compound of formula (I) or (Ia) or a salt thereof in a form suitable for administration to humans. Administration is preferably carried out by injection of the formulation as an aqueous solution. Such a formulation may optionally contain further ingredients such as buffers; pharmaceutically acceptable solubilisers (e.g. cyclodextrins or surfactants such as Pluronic, Tween or phospholipids); pharmaceutically acceptable stabilisers or antioxidants (such as ascorbic acid, gentisic acid or para-aminobenzoic acid).

The dose of a compound of formula (I), (Ia) or a salt thereof will vary depending on the exact compound to be administered, the weight of the patient, and other variables as would be apparent to a physician skilled in the art. Generally, the dose would lie in the range 0.1 nmol/kg to 50 nmol/kg, preferably 1 nmol/kg to 5 nmol/kg.

A compound of formula (I), (Ia), or a salt or solvate thereof may be prepared from the corresponding compound of formula (II):

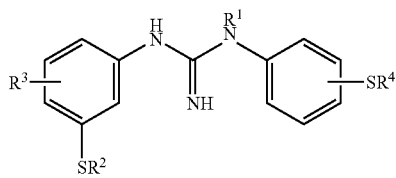

wherein one of $R^2$ or $R^4$ is hydrogen or a thiol protecting group such as benzyl, and the other is hydrogen, $C_{1-4}$ alkyl, or a thiol protecting group such as benzyl; $R^1$ is hydrogen or $C_{1-4}$alkyl, and $R^3$ is halo; by (i) removal of any thiol protecting groups, and (ii) reaction with the appropriate alkylhalide $[^{11}C]C_{1-4}$alkyl-X or $[^{18}F]$—$C_{1-4}$fluoroalkyl-Y, wherein X and Y are independently halo, preferably chloro, iodo, or bromo, or another suitable leaving group such as an aryl or alkyl sulphonate, for example, tosylate, triflate, or mesylate.

This reaction with the alkylhalide is preferably carried out in a suitable solvent such as N,N-dimethylformamide (DMF), acetone, dichloromethane, chloroform, dimethylsulphoxide, methanol, ethanol, propanol, isopropanol, tetrahydrofuran, or acetonitrile and in the presence of a base, suitably an inorganic base such as potassium carbonate, potassium hydroxide, or sodium hydride, or an organic base such as a trialkylamine, for example triethylamine, diisopropylethylamine, or dimethylaminopyridine.

The compounds of formula (II) are useful intermediates for preparation of PET tracers of formula (I) and, as such, form a further aspect of the invention.

According to a further aspect of the invention there is provided a process for preparation of a compound of formula (I):

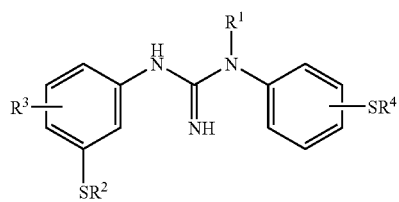

or a salt or solvate thereof, wherein:

$R^1$ is hydrogen or $C_{1-4}$alkyl;

$R^2$ and $R^4$ are each independently selected from $C_{1-4}$ alkyl, $[^{11}C]$—$C_{1-4}$alkyl, and $[^{18}F]$—$C_{1-4}$ fluoroalkyl provided that at least one of $R^2$ and $R^4$ is $[^{11}C]$—$C_{1-4}$alkyl or $[^{18}F]$—$C_{1-4}$ fluoroalkyl; and $R^3$ is halo;

which comprises reaction of a compound of formula (II):

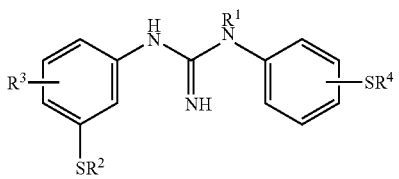

wherein one of $R^2$ or $R^4$ is hydrogen or a thiol protecting group such as benzyl, and the other is hydrogen, $C_{1-4}$ alkyl, or a thiol protecting group such as benzyl; $R^1$ is hydrogen or $C_{1-4}$alkyl, and $R^3$ is halo;

by (i) removal of any thiol protecting groups, and (ii) reaction with the appropriate alkylhalide $[^{11}C]C_{1-4}$alkyl-X or $[^{18}F]$—$C_{1-4}$-fluoroalkyl-Y, wherein X and Y are independently halo, preferably chloro, iodo, or bromo, or another suitable leaving group such as an aryl or alkyl sulphonate, for example, tosylate, triflate, or mesylate;

in a suitable solvent and in the presence of a base.

According to a further aspect of the invention there is provided a kit for the preparation of a radiopharmaceutical formulation comprising a compound of formula (II) as defined above. In use of the kit, the compound of formula (II) would be converted to the corresponding compound of formula (I) using the process described above.

Compounds of formula (II) in which $R^2$ is hydrogen or a thiol protecting group may be prepared from a compound of formula (III) or a salt thereof:

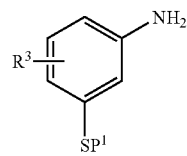

wherein $R^3$ is halo and $P^1$ is a thiol protecting group as described below; by reaction with a compound of formula (IV):

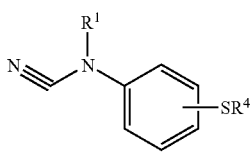
(IV)

wherein R¹ is hydrogen or $C_{1-4}$alkyl and R⁴ is as defined for the desired compound of formula (II). The coupling of compound of formula (III) with a compound of formula (IV) may be performed without solvent, or in the presence of a high boiling non-protic solvent such as chlorobenzene, toluene, or xylene. This reaction may be effected at elevated temperature, for example 50 to 200° C., suitably at around 160° C. Following reaction, the protecting group P¹ may be removed as described below.

Suitable thiol group protection and deprotection methodologies may be found, for example, in Protecting Groups in Organic Synthesis, Theodora W. Greene and Peter G. M. Wuts, published by John Wiley & Sons Inc. Suitable thiol protecting groups include arylalkyl groups such as benzyl or para-methoxybenzyl which may be removed before performing the radiolabelling step, for example by treatment with an acid for example a Lewis Acid such as $AlCl_3$.

The synthesis of a compound of formula (II) from compounds of formula (III) and (IV) is illustrated in Scheme 1.

Scheme 1

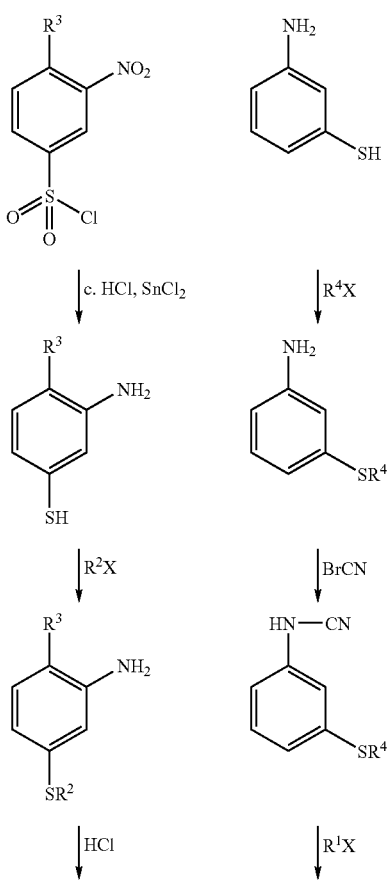

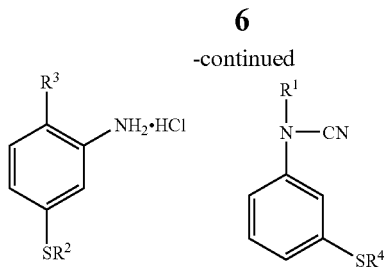

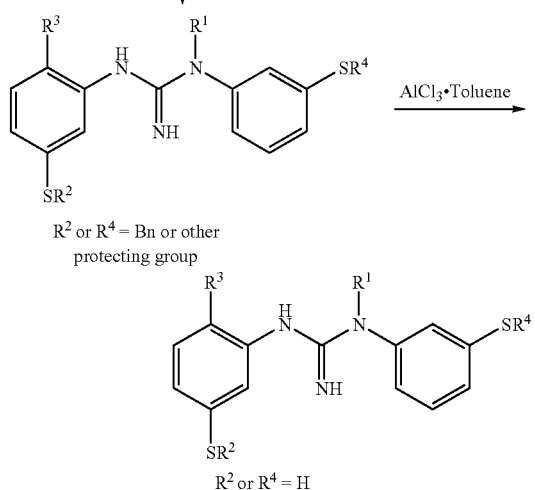

Compounds of formula (III) and (IV) may be prepared from commercially available starting materials using methods according to or analogous to those described in Scheme 1 and the Examples.

Compounds of formula (II) in which R⁴ is hydrogen or a thiol protecting group may be prepared from a compound of formula (V):

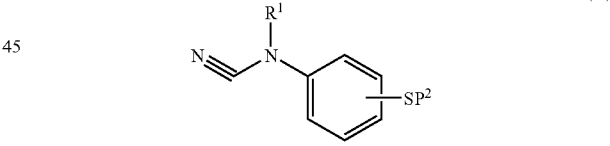
(V)

wherein R¹ is hydrogen or $C_{1-4}$alkyl and P² is a thiol protecting group as described above; by reaction with a compound of formula (VI):

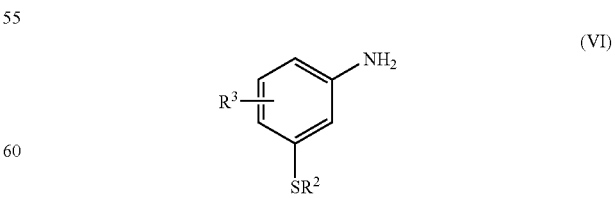
(VI)

wherein R³ is halo and R² is as defined for the desired compound of formula (II). The coupling of a compound of formula (V) with a compound of formula (VI) may be performed by methods analogous to those described for the coupling of a compound of formula (III) with a compound of formula (IV). Following reaction, the protecting group $P^2$ may be removed as described above.

This synthesis of a compound of formula (II) from compounds of formula (V) and (VI) is illustrated in Scheme 2.

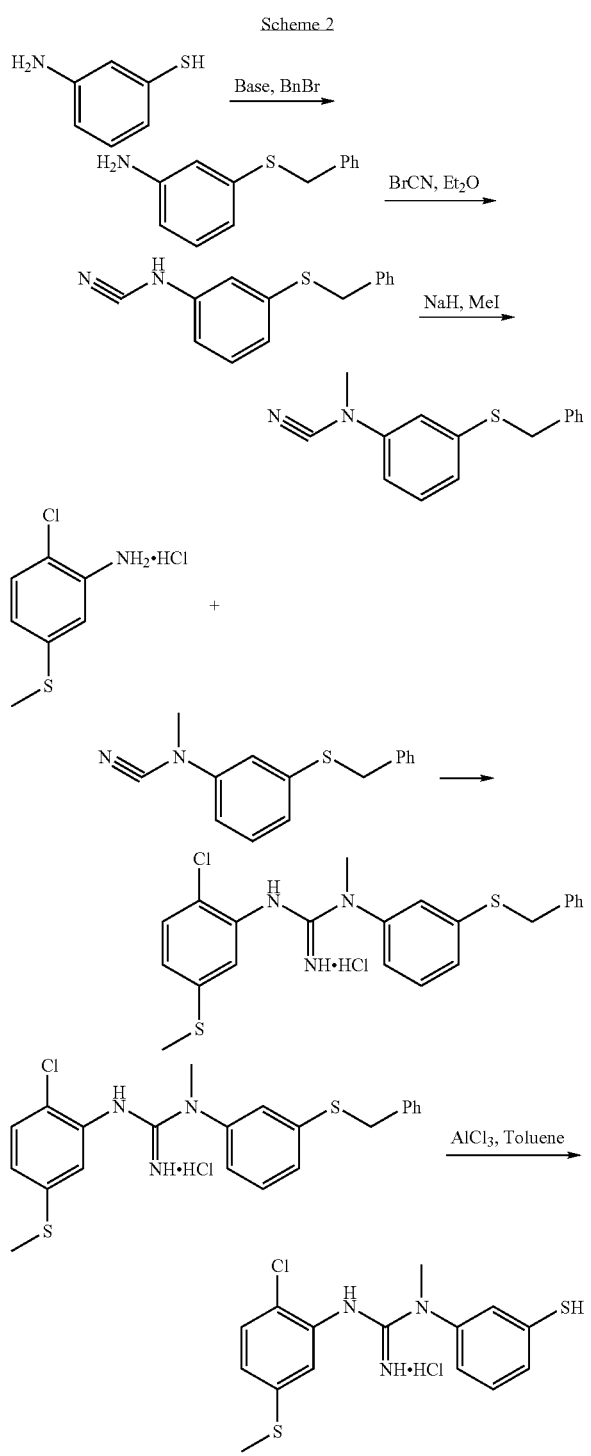

Compounds of formula (V) and (VI) may be prepared from commercially available starting materials using methods according to or analogous to those described in Scheme 2 and the Examples.

The invention will now be illustrated by way of the Examples in which the following abbreviations are used:
HPLC: high performance liquid chromatography
UV: ultraviolet
TLC: thin layer chromatography
EtOAc: ethyl acetate
IR: infrared
min(s): minute(s)

EXAMPLE 1

Synthesis of N-(2-Chloro-5-fluoromethylthio)-phenyl-N'-(3-methylthio)-phenyl-N'-methylguanidine Example 1(i)

Synthesis of 3-amino-4-chlorobenzene thiol

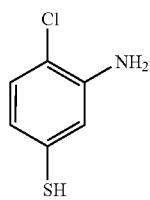

To a cooled solution (0° C.) of tin(II) chloride (11.260 g, 59.40 mmol) in 10 ml concentrated hydrochloric acid was slowly added 4-chloro-3-nitro-benzenesulfonyl chloride (1.690 g, 6.60 mmol) portionwise. The resulting suspension was kept cool and stirred for 15 minutes before the mixture was heated to reflux for 1 hour. After cooling to room temperature the mixture was diluted with water (100 ml) and carefully neutralised using $NaHCO_3$. The aqueous phase was extracted with chloroform (4×50 ml) and the organic phase separated and dried over $Na_2SO_4$. Removal of solvent under vacuum afforded a bright yellow solid. Column chromatography on silica gel using 1:1 chloroform/hexane as the mobile phase afforded 3-amino-4-chlorobenzene thiol as a white solid (0.632 g, 60%).

$^1$H NMR $\delta(CDCl_3)$ 7.08 (d, 1H, |J|=8.5 Hz, aryl H), 6.67 (d, 1H, |J|=2.0 Hz, aryl H), 6.59 (dd, 1H, |J|=8.5 and 2.0 Hz, aryl H), 4.03 (br s, 2H, $NH_2$), 3.37 (s, 1H, SH).

Example 1(ii)

Synthesis of (5-Benzylthio-2-chloro)-aniline and (5-Benzylthio-2-chloro)-aniline HCl salt

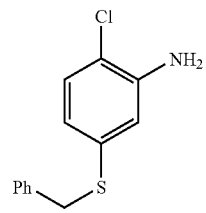

To a cooled solution (0° C.) of 3-Amino-4-chlorobenzene thiol (0.630 g, 3.92 mmol) in anhydrous tetrahydrofuran (THF) (15 ml) was added n-butyllithium (1.6 M in hexanes, 2.45 ml, 3.92 mmol) and the reaction mixture stirred rapidly.

To this mixture was slowly added benzylbromide (0.47 ml, 3.92 mmol) and the reaction mixture stirred rapidly, warming to room temperature over circa. 1 hour. Removal of the solvent under reduced pressure afforded a crude product which was purified by column chromatography on silica gel using 1:1 dichloromethane/hexane as the mobile phase. (5-Benzylthio-2-chloro)-aniline was isolated as a bright white solid (0.805 g, 82%).

$^1$H NMR δ(CDCl$_3$) 7.26 (m, 3H, phenyl H), 7.22 (br m, 2H, phenyl H), 7.09 (d, 1H, |J|=8.3 Hz), 6.66 (d, 1H, |J|=1.9 Hz), 6.61 (dd, |J|=8.3 and 1.9 Hz), 4.04 (s, 2H, CH$_2$), 4.03 (br s, 2H, NH$_2$).

To a cooled solution (0° C.) of (5-Benzylthio-2-chloro)-aniline (0.805 g, 3.21 mmol) in anhydrous diethylether (10 ml) was slowly added anhydrous hydrochloric acid in diethylether (1M, 5.0 ml, 5 mmol). The resulting precipitate was isolated by filtration, washed with diethylether (2×5 ml) and dried under vacuum. (5-Benzylthio-2-chloro)-aniline HCl salt was isolated in near quantitative yield as a white solid (0.865 g, 94%).

Example 1(iii)

Synthesis of Methyl-(3-methylthio-phenyl)-cyanamide

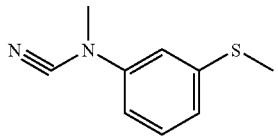

To a cooled solution (0° C.) of 3-Methylthio-aniline (1.850 g, 13.30 mmol) in anhydrous diethylether (10 ml) was added a diethylether solution (10 ml) of cyanogen bromide (0.704 g, 6.65 mmol). CAUTION: Cyanogen bromide is highly toxic. The resulting solution was allowed to stir at room temperature over night. The resulting mixture was filtered to remove the precipitate and the diethylether filtrate was washed with 1M HCl (20 ml) and brine (20 ml) before the solvent was removed under vacuum to yield an oily yellow residue. Purification of the crude product by column chromatography on silica gel using 95:5 dichloromethane/ethyl acetate afforded (3-methylthio-phenyl)-cyanamide as a near colourless oil which crystallised on standing (0.570 g, 52%).

A flame-dried Schlenk flask under a nitrogen atmosphere was charged with sodium hydride (60% in mineral oil, 0.14 g, 3.5 mmol), 3-Methylsulfanyl-phenyl-cyanamide (0.493 g, 3.00 mmol) and anhydrous THF (5 ml). The mixture was stirred rapidly and heated to 70° C. for circa 0.5 hours. On cooling to room temperature, iodomethane (0.37 ml, 6.00 mmol) was added drop wise and the mixture stirred at room temperature over night. The resulting clear, colourless solution was concentrated under vacuum before water (30 ml) and diethylether (40 ml) were added. The organic phase was separated, dried over Na$_2$SO$_4$ and the diethylether solvent removed under vacuum to yield a crude residue. Purification by column chromatography on silica gel using dichloromethane as mobile phase afforded the title compound as a pale yellow oil (0.388 g, 73%).

$^1$H NMR δ (CDCl$_3$) 7.26 (m, 1H, aryl H), 6.96 (m, 2H, aryl H), 6.81 (m, 1H, aryl H), 3.31 (s, 3H, NCH$_3$), 2.48 (s, 3H, SCH$_3$).

Example 1(iv)

Synthesis of N-(5-Benzylthio-2-chloro)-phenyl-N'-(3-methylthio)-phenyl-N'-methylguanidine HCl salt

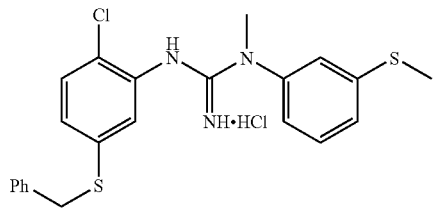

To a flame-dried 10 ml round bottomed flask equipped with a magnetic stir bar was added methyl-(3-methylthio-phenyl)-cyanamide (0.185 g, 1.04 mmol) and (5-benzylthio-2-chloro)-aniline HCl salt (0.297 g, 1.04 mmol). The flask was evacuated and refilled with nitrogen three times before the flask was sealed under nitrogen and heated to 160° C. for 3 hours. On cooling to room temperature the pale orange residue was taken up in a minimum volume of dichloromethane (0.5-1 ml) and purified by column chromatography on silica gel using a 0-10% gradient of methanol in dichloromethane. Removal of solvent under high vacuum afforded the title compound as a glassy white solid (0.357 g, 74%).

$^1$H NMR δ (d$_6$-DMSO) 9.70 (br s, 1H, NH), 8.01 (br s, 1H, NH), 7.39-7.08 (m, 11H, aryl H), 7.09 (m, 1H, aryl H), 4.24 (s, 2H, CH$_2$), 3.39 (s, 3H, N—CH$_3$), 2.45 (s, 3H, S—CH$_3$).

Example 1(v)

Synthesis of N-(2-Chloro-5-mercapto)-phenyl-N'-(3-methylthio)-phenyl-N'-methylguanidine HCl salt

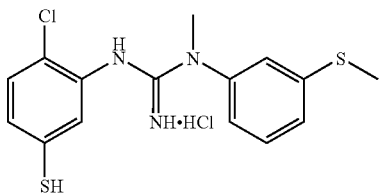

A flame-dried Schlenk flask under a nitrogen atmosphere was charged with aluminium chloride (0.293 g, 2.20 mmol) and anhydrous toluene (5 ml). To the resulting stirred suspension was added a toluene solution of N-(5-Benzylthio-2-chloro)-phenyl-N'-(3-methylthio)-phenyl-N'-methylguanidine HCl salt (0.250 g, 0.54 mmol) and the reaction mixture stirred rapidly at room temperature for 2 hours. The resulting mixture was diluted with methanol (5 ml) which resulted in a colourless, homogeneous solution. Removal of solvents under vacuum afforded a colourless residue which was taken up into dichloromethane (3 ml), filtered and the filtrate purified by column chromatography on silica gel using a 0-10% gradient of methanol in dichloromethane. The title compound was isolated as a glassy white solid (0.130 g, 64%).

A sample of the free-base was prepared by heating the HCl salt in the presence of K$_2$CO$_3$ in acetone, followed by isolation by column chromatography on silica gel using a 0-10% gradient of methanol in dichloromethane.

$^1$H NMR δ (CDCl$_3$) 7.29 (br s, 1H, aryl H), 7.28 (m, 1H, aryl H), 7.13 (m, 2H, aryl H), 7.11 (d m, 1H, aryl H), 7.06 (dd, 1H, aryl H), 7.01 (d m, 1H, aryl H), 3.48 (br s, 1H, SH), 3.36 (s, 3H, NCH$_3$), 2.49 (s, 3H, SCH$_3$).

Example 1(vi)

Synthesis of N-(2-Chloro-5-fluoromethylthio)-phenyl-N'-(3-methylthio)-phenyl-N'-methylguanidine

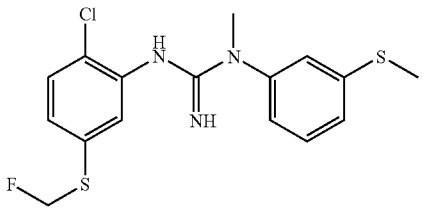

A flame-dried Schlenk flask under a nitrogen atmosphere was charged with N-(2-chloro-5-mercapto)-phenyl-N'-(3-methylthio)-phenyl-N'-methylguanidine HCl salt (0.037 g, 0.10 mmol), triethylamine (0.020 g, 0.20 mmol) and anhydrous dichloromethane (2-3 ml) and cooled in an ice-bath to 0° C. Fluorobromomethane gas was bubbled through the dark coloured reaction mixture for 30 seconds before the reaction was allowed to slowly warm to room temperature. After 2 hours, the resulting pale yellow solution was concentrated under vacuum to yield a crude residue which was re-dissolved in dichloromethane (1 ml) and purified by column chromatography on silica gel using a 0-10% gradient of methanol in dichloromethane. Removal of solvent under high vacuum afforded the title compound as a pale yellow oil (0.024 g, 68%).

$^1$H NMR δ (CDCl$_3$) 7.32 (m, 2H, aryl H), 7.20 (m, 1H, aryl H), 7.17 (m, 1H, aryl H), 7.16-7.06 (m, 2H, aryl H), 7.04 (m, 1H, aryl H), 5.71 (d, 2H, |J|=52.8 Hz, CH$_2$F), 3.41 (s, 3H, N—CH$_3$), 2.50 (s, 3H, S—CH$_3$).

Example 2

N-(2-Chloro-5-[$^{18}$F]fluoromethylthio)-phenyl-N'-(3-methylthio)-phenyl-N'-methylguanidine The title compound was prepared using methods analogous to those in Example 1(vi) but using [$^{18}$F]fluorobromomethane as the haloalkylating agent, anhydrous acetonitrile as the solvent and cesium carbonate as the base. The identity of the product was confirmed by HPLC co-elution of N-(2-Chloro-5-[$^{18}$F]-fluoromethylthio)-phenyl-N'-(3-methylthio)-phenyl-N'-methylguanidine with an authentic sample prepared in Example 1(vi).

HPLC Method

With HPLC analytical conditions tested, it was found that the most efficient chromatographic separation between precursor N-(2-chloro-5-thio)phenyl-N'-3'-(methylthio)-phenyl-N'-methylguanidine and reference standard N-(2-Chloro-5-fluoromethylthio)-phenyl-N'-(3-methylthio)-phenyl-N'-methylguanidine was as follows: 5μ-Luna C-18(2) column (250×4.6 mm), MP 55/45 acetonitrile/0.01M (NH$_4$)$_2$HPO$_4$, flow rate at 1 ml/min, UV 254 nm. The retention time for N-(2-chloro-5-thio)phenyl-N'-3'-(methylthio)-phenyl-N'-methylguanidine precursor was 20.0 minutes, while N-(2-Chloro-5-fluoromethylthio)-phenyl-N'-(3-methylthio)-phenyl-N'-methylguanidine had a retention time of 9.70 minutes.

Example 3

Synthesis of N-(2-Chloro-5-(2-fluoro-ethylthio))-phenyl-N'-(3-methylthio)-phenyl-N'-methylguanidine

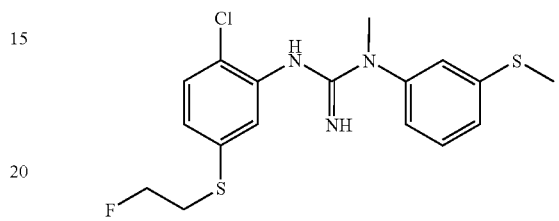

To a flame-dried Schlenk flask fitted with a reflux condenser was charged with N-(2-Chloro-5-mercapto)-phenyl-N'-(3-methylthio)-phenyl-N'-methylguanidine HCl salt (0.030 g, 0.08 mmol), potassium carbonate (0.022 g, 0.16 mmol) and anhydrous acetone (2 ml). To the mixture was added a solution of 2-fluoroethyltosylate (0.017 g, 0.080 mmol) in acetone (1 ml) and the reaction heated to reflux under a nitrogen atmosphere for 3 days. After cooling to room temperature the solvent was removed under vacuum and the residue re-dissolved in dichloromethane (1 ml). Purification by column chromatography on silica gel using a 0-10% gradient of methanol in dichloromethane afforded the title compound as pale yellow oil (0.021 g, 68%).

$^1$H NMR δ (CDCl$_3$) 7.30 (m, 2H, aryl H), 7.19 (br m, 1H, aryl H), 7.13 (br m, 3H, aryl H), 6.94 (m, 1H, aryl H), 4.53 (dt, 2H, |J|=6.6 and 47.0 Hz, CH$_2$F), 3.41 (s, 3H, N—CH$_3$), 3.12 (dt, 2H, |J|=6.6 and 20.5 Hz), 2.51 (s, 3H, S—CH$_3$).

Example 4

Synthesis of N-(2-Chloro-5-(2-[$^{18}$F]fluoro-ethylthio))-phenyl-N'-(3-methylthio)-phenyl-N'-methylguanidine The title compound was prepared using methods analogous to those in Example 3 but using 2-[$^{18}$F]fluoroethyltosylate as the haloalkylating agent, a 1:2 mixture of anhydrous acetonitrile/ethanol as the solvent and cesium carbonate as the base. The identity of the product was confirmed by HPLC co-elution of N-(2-Chloro-5-[$^{18}$F]fluoroethylthio)-phenyl-N'-(3-methylthio)-phenyl-N'-methylguanidine with an authentic sample prepared in Example 3.

HPLC Method

With HPLC analytical conditions tested, it was found that the most efficient chromatographic separation between precursor N-(2-chloro-5-thio)phenyl-N'-3'-(methylthio)-phenyl-N'-methylguanidine and reference standard N-(2-Chloro-5-(2-fluoro-ethylthio))-phenyl-N'-(3-methylthio)-phenyl-N'-methylguanidine was as follows: 5μ-Luna C-18(2) column (250×4.6 mm), MP 55/45 acetonitrile/0.01M (NH$_4$)$_2$HPO$_4$, flow rate at 1 ml/min, UV 254 nm. The retention time for N-(2-chloro-5-thio)phenyl-N'-3'-(methylthio)-phenyl-N'-methylguanidine precursor was 20.0 minutes, while N-(2-

Chloro-5-fluoroethylthio)-phenyl-N'-(3-methylthio)-phenyl- had a retention time of 9.40 minutes.

Example 5

Synthesis of N-(2-Chloro-5-(2-[$^{11}$C]ethylthio))-phenyl-N'-(3-methylthio)-phenyl-N'-methylguanidine The title compound is prepared using methods analogous to those in Example 6 but using 2-[$^{11}$C]iodoethane as the haloalkylating agent.

Example 6

Synthesis of N-(2-Chloro-5-methylthio)-phenyl-N'-(3-methylthio)-phenyl-N'-methylguanidine

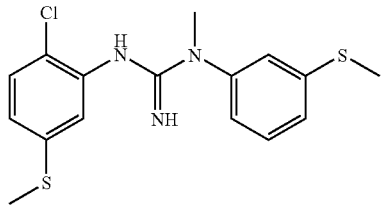

To a round bottom flask equipped with a magnetic stirrer was added sodium methoxide (1.4 mg, 26.6 umol), N-(2-chloro-5-mercapto)-phenyl-N'-(3-methylthio)-phenyl-N'-methylguanidine HCl salt (5.0 mg, 13.3 umol) and anhydrous methanol (1 ml). The reaction mixture was stirred rapidly under a nitrogen atmosphere for 5 minutes before the mixture was further treated with iodomethane (1.8 ul, 30 umol). After stirring at room temperature for 15 minutes the solvent was removed under vacuum and the residue submitted for analysis by HPLC.

Example 7

Synthesis of N-(2-Chloro-5-[$^{11}$C]methylthio)-phenyl-N'-(3-methylthio)-phenyl-N'-methylguanidine The title compound is prepared using methods analogous to those in Example 6 but using [$^{11}$C]iodomethane as the methylating agent.

Example 8

Synthesis of N-(2-Chloro-5-methylthio)-phenyl-N'-(3-methylthio)-phenyl-N'-methylguanidine

Example 8(i)

Synthesis of 2-chloro-5-(methylthio)aniline hydrochloride

To a stirred solution of 2-chloro-5-(methylthio)benzoic acid (5 g, 24.67 mmol) in t-butanol (20 mL) was added triethylamine (5.25 mL, 37.8 mmol). After stirring briefly, diphenylphosphoryl azide (6 mL, 27.60 mmol) was added drop wise. The reaction mixture was slowly heated to reflux for 6 hours and then cooled to room temperature. The solvent was removed under reduced pressure and the crude reaction mixture was dissolved in tetrahydrofuran (12.5 mL) followed by the addition of 12.5 mL trifluoroacetic acid (1:1). The reaction mixture was heated to reflux for 6 hours and the solvent was evaporated after cooling to room temperature. The reaction mixture was treated with NaOH (25%) to bring the pH to 12 while cooling in an ice water bath. The product was repeatedly extracted into ethylacetate (4×25 mL) and the organic layer washed with water (10 mL). The combined extracts were dried over MgSO$_4$ and concentrated in vacuo to afford yellow oil. The product was purified by column chromatography (SiO$_2$, gradient of hexanes/EtOAc) and the collected samples dissolved in ether and treated with HCl/ether (10 mL, 1M) to provide white crystals. The title product was a white solid (3.73 g, 87% yield): mp: 180-181° C.; TLC: hexanes/EtOAc (9:1) R$_f$=0.51; MS (Cl) m/e 174 (M+1 for C$_7$H$_8$ClNS) and m/e 191 (M+NH$_3$), $^1$H-NMR (CDCl$_3$) δ (ppm) 7.2-6.7 (m, 3H, Ar—H), 2.5 (s, 3H, S—CH$_3$).

Example 8(ii)

Synthesis of 3-(benzylthio)aniline

To a stirred solution of sodium hydroxide (2.1 g, 52.5 mmol) in water (4 ml) cooled in an ice bath, a solution of 3-aminothiophenol (4.8 g, 38.4 mmol) in ethanol (20 ml) was added drop wise, followed by the addition of solution of benzyl chloride (5 g, 39.5 mmol) in ethanol (5 ml). After the addition, the reaction mixture was stirred at room temperature for 4 hours and became a brown solution with white precipitate. After filtering off the precipitate, the filtrate was concentrated and residue was taken by dichloromethane (40 ml). The dichloromethane solution was washed with aqueous sodium hydroxide solution three times (0.5 M, 3×40 ml) and water once (40 ml). After dried over MgSO$_4$ and filtered, dichloromethane solution was then concentrated in vacuo to afford thick yellow oil as crude product. It was further purified by flash chromatography (SiO$_2$, hexanes/CH$_2$Cl$_2$, 0-100%) to afford 3-(benzylthio)aniline (6.77 g, 82%) as a pale yellow oil, which solidified into white solid after staying at room temperature. Thin layer chromatography: Dichloromethane, R$_f$=0.37; $^1$H-NMR (CDCl$_3$) δ(ppm) 6.6-7.4 (m, 9H, Ar—H), 4.15 (s, 2H, S—CH2).

Example 8(iii)

Synthesis of 3-(benzylthio)phenylcyanamide

A solution of cyanogen bromide (1.42 g, 13.4 mmol) in anhydrous diethyl ether (10 ml) was added slowly to a stirred solution of 3-(benzylthio)aniline (4.6 g, 21.4 mmol) in anhydrous diethyl ether (25 ml) at 0-4° C. After the addition, the reaction mixture was stirred at room temperature for 12 hours and became a brown solution with a white precipitate. The precipitate was filtered off and the filtrate was washed with aqueous HCl (1 M, 3×40 ml) and followed by brine (40 ml). The ether solution was dried over MgSO$_4$, filtered, and concentrated in vacuo to yield yellow oil as crude product. It was further purified by flash chromatography (SiO$_2$, CH$_2$Cl$_2$/EtOAc, 0-20%) to afford 3-(benzylthio)phenylcyanamide (2.82 g, 55% yield) as a white solid: TLC: Dichloromethane/EtOAc (93:7), R$_f$=0.64; $^1$H-NMR (CDCl$_3$) δ (ppm) 7.2-6.7 (m, 9H, Ar—H), 4.12 (s, 2H, S—CH$_2$). IR(KBr): 3178 cm$^{-1}$ (secondary N—H), 3023-3085 cm$^{-1}$ (C—H aromatic stretch), 2227 cm$^{-1}$ (CN).

Example 8(iv)

Synthesis of 3-(benzylthio)phenyl-N-methylcyanamide

To a solution of 3-(benzylthio)phenylcyanamide (0.80 g, 3.33 mmol) dissolved in acetonitrile (8 mL) was added diisopropylethylamine (0.65 g, 5.0 mmol), followed by addition of methyl iodide (0.94 g, 6.66 mmol). The reaction mixture was refluxed at 80-85° C. for 3 hours. After removal of solvents the residue was taken by dichloromethane (40 ml) and the organic solution was washed by water (40 ml). After dried over $MgSO_4$ and filtered, dichloromethane solution was then concentrated in vacuo to afford yellow oil as crude product. Purification by column chromatography ($SiO_2$, Hexane/$CH_2Cl_2$, 50% to 100%) to afford 3-(benzylthio)phenyl-N-methylcyanamide as a pale yellow oil (0.67, 80% yield): $CH_2Cl_2$ $R_f$=0.45; $^1$H-NMR ($CDCl_3$) δ (ppm) 7.3-6.8 (m, 9H, Ar—H), 4.06 (s, S—$CH_2$, 2H), 3.57 (s, 3H, N—$CH_3$).

Example 8(v)

Synthesis of N-(2-chloro-5-methylthio)-phenyl-N'-3'-(benzylthio)-phenyl-N'-methylguanidine To a dried 25 ml flask assembled with water condenser, 3-(benzylthio)phenyl-N-methylcyanamide (0.65 g, 2.56 mmol), 2-chloro-5-(methylthio)aniline hydrochloride (0.54 g, 2.56 mmol) and 1 ml of chlorobenzene were added. The flask was then flushed through with nitrogen gas and then heated at 150° C. for 3 hours while stirring. The reaction mixture was cooled to room temperature. After removal of chlorobenzene in vacuo thick glassy oil was left as the crude product. Purification by flash chromatography ($SiO_2$, $CH_2Cl_2$/MeOH, 0-20%) to yield the guanidine hydrochloride (0.9 g, 85% yield) as a solid: thin layer chromatography: $CH_2Cl_2$/MeOH (9:1), $R_f$=0.34; $^1$H NMR ($CDCl_3$) δ (ppm) 6.8-7.3 (m, 12H, Ar—H), 4.06 (s, S—$CH_2$, 2H), 3.57 (s, 3H, N—$CH_3$), 2.35 (s, 3H, S—$CH_3$).

Example 8(vi)

Synthesis of N-(2-chloro-5-methylthio)-phenyl-N'-3'-thiophenyl-N'-methylguanidine To a 25 ml dried flask, aluminium trichloride (125 mg, 0.94 mmol) was added under nitrogen protection, followed by drop wise addition of N-(2-chloro-5-methylthio)-phenyl-N'-3'-(benzylthio)-phenyl-N'-methylguanidine (100 mg, 0.23 mmol) in toluene (2 ml). The mixture was stirred under nitrogen at room temperature overnight. The reaction was quenched by using acetic acid (0.5 ml) and then concentrated in vacuo to afford thick oil as crude product. Purification by flash chromatography ($SiO_2$, $CH_2Cl_2$/MeOH, 0-20%) to yield the title product (70 mg, 96% yield) as a glassy solid: TLC: $CH_2Cl_2$/MeOH (9:1), $R_f$=0.14; $^1$H NMR ($CDCl_3$) δ (ppm) 6.8-7.3 (m, 7H, Ar—H), 3.35 (s, 3H, N—$CH_3$), 2.4 (s, 3H, S—$CH_3$).

Example 8(vii)

Synthesis of N-(2-Chloro-5-methylthio)-phenyl-N'-(3-methylthio)-phenyl-N'-methylguanidine HPLC Method With HPLC analytical conditions tested, it was found that the most efficient chromatographic separation between precursors N-(2-chloro-5-methylthio)-phenyl-N'-3'-thiophenyl-N'-methylguanidine, N-(2-chloro-5-thio)phenyl-N'-3'-(methylthio)-phenyl-N'-methylguanidine and reference standard N-(2-chloro-5-methylthio)-phenyl-N'-3'-(methylthio)-phenyl-N'-methylguanidine was as follow: μ-Bondapak C-18 column (300×7.8 mm), MP 60/40 acetonitrile/0.05M $(NH_4)_2HPO_4$, flow rate at 2 ml/min, UV 254 nm. The retention times for 3'-desmethylthio- and 5-desmethylthio precursors were 6.65 min and 6.01 minutes, respectively, while N-(2-chloro-5-methylthio)phenyl-N'-(3-methylthio)phenyl-N'-methylguanidine had a retention time of 11.81 minutes.

Methyl iodide (0.3-0.6 mg, 1-2 equivalence to precursor) was added into the solution containing N-(2-chloro-5-methylthio)-phenyl-N'-3-thiophenyl-N'-methylguanidine (0.5-0.8 mg), potassium butoxide (0.5-1.0 mg, 2-4 equivalence to precursor) in either N,N-dimethylformamide or in anhydrous ethanol (250-350 μl). The resulting mixture was stirred at room temperature for 5 minutes and then quenched by addition of 100 μl of HPLC mobile phase (0.05M $(NH_4)_2HPO_4$). An aliquot of reaction mixture was taken and injected onto HPLC column for analysis. Based on results from HPLC analysis, it was shown that the title product was produced in a yield higher than 75% with either N,N-dimethylformamide or ethanol used as solvents in all test experiments, chemistry worked well in a consistent manner and the separation between the title product and its desmethylthio-precursor was efficient enough for a semi-preparative separation in hot chemistry.

Example 9

Synthesis of N-(2-chloro-5-methylthio)-phenyl-N'-(3-[$^{11}$C]methylthio)-phenyl-N'-methylguanidine

[$^{11}$C] Methyl iodide, which was produced by reduction of [$^{11}$C] $CO_2$ using lithium aluminium hydride, followed by iodination using hydriodic acid and distillation, was trapped into a vial containing N-(2-chloro-5-methylthio)-phenyl-N'-3-thiophenyl-N'-methylguanidine (0.5 mg), potassium butoxide (0.8 mg) in N,N-dimethylformamide (300 μl). The labelling chemistry was carried out at room temperature for 5 minutes and reaction mixture was quenched by the addition of 100 μl of HPLC mobile phase (0.05M $(NH_4)_2HPO_4$). An aliquot sample was taken from the reaction mixture and injected onto in a radioactive HPLC system. The analysis was carried out at the same chromatographic conditions as used in Example 8. The radioactive peak, which eluted with retention time of 11.81 minutes, was confirmed to be the title product by co-eluting with cold reference standard at the same analytical condition. The decay corrected radiochemical yield for the title product, based on [$^{11}$C]methyl iodide, was found to be higher than 90%. The total time for the radiosynthesis, starting from [$^{11}$C] $CO_2$, was within 20 minutes after end of cyclotron bombardment.

BIOLOGICAL EXAMPLES

Biodistribution data for N-(2-Chloro-5-(2-[$^{18}$F]-fluoro-ethylthio))-phenyl-N'-(3-methylthio)-phenyl-N'-methylguanidine

Materials and Methods

N-(2-Chloro-5-(2-[$^{18}$F]fluoro-ethylthio))-phenyl-N'-(3-methylthio)-phenyl-N'-methylguanidine was prepared according to Example 4 (synthesis formulation ~3% ethanol in 0.9% w/v saline solution) with a radiochemical purity of ~99% and, at time of injection, the specific activity ranged from 4-16 GBq/nmol$^{-1}$. Biodistribution and blood data were from 11 adult male Sprague-Dawley rats (body weight range, 269 to 329 g; mean±S.E.=300±18 g). N-(2-Chloro-5-(2-[$^{18}$F] fluoro-ethylthio))-phenyl-N'-(3-methylthio)-phenyl-N'-methylguanidine was injected directly into the tail vein of each rat whilst under isoflurane anaesthesia. Each animal was then allowed to recover from anaesthesia. At designated times after injection, rats were sacrificed by cervical dislocation under anaesthesia and brain and body tissues were rapidly sampled.

Biodistribution

The data were acquired using two syntheses. Rats were given an average of 86 MBq (85.3 MBq for first experimental day and 87.3 MBq for the second experimental day), in a volume of 0.20 ml (synthesis formulation ~3% alcohol), via direct intravenous injection through the tail vein. The mass of co-injected N-(2-Chloro-5-(2-[$^{18}$F]fluoro-ethylthio))-phenyl-N'-(3-methylthio)-phenyl-N'-methylguanidine ranged from 0.7-2.9 nmol.kg$^{-1}$. Details of the methodology, together with processing and counting of the samples can be found in Hume et al., Nucl. Med. Biol. (1991) 18: 339-351. Data were normalised for injected radioactivity and body weight, giving:

'uptake units'=(cpm.g$^{-1}$ wet weight tissue)·(injected cpm.g$^{-1}$ body weight)$^{-1}$

Results

Radioactivity concentration data are additionally collated in Tables 1 (peripheral tissue) and 2 (brain). As metabolite studies were not carried out, the proportion of the total radioactivity reflecting label associated with parent N-(2-Chloro-5-(2-[$^{18}$F]fluoro-ethylthio))-phenyl-N'-(3-methylthio)-phenyl-N'-methylguanidine is not known. Note, Blood and plasma samples were collected post-mortem from the heart ventricle.

Body Distribution

The data are summarised in Table 1. Of the tissues sampled, skeletal muscle, skin and testis showed low initial content of ~0.4 uptake units which was retained over the course of the experiment. Bone showed an initial high uptake of 1.4 which decreased to ~0.8 over the 90 minutes of the experiment suggesting no evidence of de-fluorination. High initial uptake was seen in lung (~30 uptake units) which reduced rapidly to 2 uptake units, at 90 minutes. Similar profiles were observed in kidney and heart. A slower rate of loss of radioactivity was seen in liver, spleen and intestine.

TABLE 1

Distribution of radioactivity in rat peripheral organs and body fluids as a function of time after intravenous injection of N-(2-Chloro-5-(2-[$^{18}$F]fluoro-ethylthio))-phenyl-N'-(3-methylthio)-phenyl-N'-methylguanidine.

| Tissue | 2 (n = 1) | 5 (n = 1) | 10 (n = 2) | 30 (n = 3) | 60 (n = 3) | 90 (n = 1) |
|---|---|---|---|---|---|---|
| 1 | 1.355 | 1.440 | 0.793 | 1.014 ± 0.019 | 0.944 ± 0.305 | 0.889 |
| 2 | 0.288 | 0.517 | 0.391 | 0.487 ± 0.036 | 0.410 ± 0.096 | 0.357 |
| 3 | 0.338 | 0.517 | 0.248 | 0.491 ± 0.019 | 0.435 ± 0.109 | 0.387 |
| 4 | 0.109 | 16.760 | 13.589 | 49.593 ± 30.733 | 23.375 ± 18.208 | 26.947 |
| 5 | 0.199 | 0.814 | 0.234 | 0.613 ± 0.175 | 0.405 ± 0.358 | 0.548 |
| 6 | 0.456 | 0.528 | 0.363 | 0.619 ± 0.081 | 0.605 ± 0.150 | 0.559 |
| 7 | 4.537 | 3.845 | 1.618 | 2.241 ± 0.617 | 1.841 ± 0.678 | 1.942 |
| 8 | 1.390 | 1.449 | 1.162 | 6.002 ± 3.338 | 10.518 ± 7.766 | 8.700 |
| 9 | 3.338 | 3.442 | 1.359 | 1.619 ± 0.494 | 7.291 ± 10.308 | 0.775 |
| 10 | 0.113 | 0.148 | 0.109 | 0.445 ± 0.035 | 1.176 ± 1.109 | 0.764 |
| 11 | 3.985 | 3.676 | 3.008 | 2.713 ± 0.086 | 1.675 ± 0.135 | 1.418 |
| 12 | 5.251 | 5.648 | 3.199 | 6.023 ± 0.699 | 3.659 ± 0.822 | 2.856 |
| 13 | 12.975 | 10.113 | 3.931 | 3.287 ± 0.208 | 2.429 ± 0.527 | 2.127 |
| 14 | 0.843 | 1.245 | 0.532 | 1.558 ± 0.443 | 1.227 ± 0.351 | 1.103 |
| 15 | 32.475 | 25.015 | 10.229 | 3.786 ± 0.292 | 2.387 ± 0.195 | 2.150 |
| 16 | 6.412 | 2.761 | 1.119 | 0.740 ± 0.019 | 0.505 ± 0.104 | 0.464 |
| 17 | 0.264 | 0.135 | 0.102 | 0.229 ± 0.047 | 0.222 ± 0.055 | 0.163 |

Time mins. (n = no. of data points)

No correction was made for blood volume. Data are in 'uptake units'. The key to the tissues is as follows: 1 bone, 2 skeletal muscle, 3 skin, 4 urine, 5 fat, 6 testis, 7 small intestine, 8 small intestinal content, 9 large intestine, 10 large intestinal content, 11 spleen, 12 liver, 13 kidney, 14 stomach, 15 lung, 16 heart (ventricle). Also shown for comparison are plasma data (17) at the equivalent sample times.

Brain Distribution

The data are summarised in Table 2. All tissues had a relatively high initial uptake of ~4 uptake units at 2 minutes after IV injection of the radioligand. This was followed by a gradual decrease in activity reaching ~0.4 uptake units at 90 minutes after radioligand injection. A small signal relative to cerebellum was obtained in hippocampus and cortex increasing from ~0.8 to 1.3 over the first 40 minutes, and falling thereafter to 1 by 90 minutes.

Peripheral clearance of N-(2-Chloro-5-(2-[$^{18}$F]-fluoro-ethylthio))-phenyl-N'-(3-methylthio)-phenyl-N'-methylguanidine was via kidney to urine and via the intestine. Rat brain showed a high uptake of radioactivity at the earliest sample time (2 min) after IV injection of N-(2-Chloro-5-(2-[$^{18}$F]-fluoro-ethylthio))-phenyl-N'-(3-methylthio)-phenyl-N'-methylguanidine. Differential heterogeneity was difficult to detect due to the physiological 'closed' or resting state of the receptors. As cerebellum showed the lowest retention after ~60 min, a small signal was seen in hippocampus (an area of known high NMDA receptor density; Bowery et al., (1988) Br. J. Pharmacol. 93: 944-954) when data were expressed relative to cerebellum radioactivity.

TABLE 2

Distribution of radioactivity in rat brain tissue as a function of time after intravenous injection of N-(2-Chloro-5-(2-[$^{18}$F]fluoroethylthio))-phenyl-N'-(3-methylthio)-phenyl-N'-methylguanidine.

| Tissue | Time mins. (n = no. of data points) | | | | | |
| --- | --- | --- | --- | --- | --- | --- |
| | 2 (n = 1) | 5 (n = 1) | 10 (n = 2) | 30 (n = 3) | 60 (n = 3) | 90 (n = 1) |
| 1 | 2.826 | 3.062 | 1.300 | 0.981 ± 0.235 | 0.504 ± 0.062 | 0.504 |
| 2 | 2.766 | 2.442 | 1.404 | 0.941 ± 0.086 | 0.502 ± 0.095 | 0.383 |
| 3 | 3.397 | 2.443 | 1.275 | 1.076 ± 0.250 | 0.533 ± 0.115 | 0.466 |
| 4 | 4.460 | 2.566 | 1.353 | 1.415 ± 0.203 | 0.553 ± 0.108 | 0.551 |
| 5 | 3.808 | 3.099 | 1.649 | 1.168 ± 0.042 | 0.519 ± 0.105 | 0.414 |
| 6 | 2.306 | 1.817 | 1.433 | 1.101 ± 0.202 | 0.481 ± 0.136 | 0.485 |
| 7 | 3.531 | 2.772 | 1.588 | 1.037 ± 0.103 | 0.517 ± 0.107 | 0.376 |
| 8 | 2.864 | 2.250 | 1.396 | 1.088 ± 0.142 | 0.548 ± 0.119 | 0.391 |
| 9 | 4.008 | 2.883 | 1.651 | 1.041 ± 0.067 | 0.541 ± 0.124 | 0.423 |
| 10 | 6.716 | 3.292 | 1.539 | 0.841 ± 0.084 | 0.456 ± 0.079 | 0.306 |
| 11 | 4.977 | 3.541 | 1.677 | 1.086 ± 0.286 | 0.486 ± 0.101 | 0.386 |
| 12 | 3.678 | 2.877 | 1.530 | 1.110 ± 0.129 | 0.551 ± 0.143 | 0.406 |
| 13 | 4.204 | 2.761 | 1.451 | 0.919 ± 0.110 | 0.454 ± 0.082 | 0.366 |
| 17 | 0.264 | 0.135 | 0.102 | 0.229 ± 0.047 | 0.222 ± 0.055 | 0.163 |
| 18 | 0.288 | 0.261 | 0.146 | 0.269 ± 0.042 | 0.229 ± 0.068 | 0.180 |

Data are in 'uptake units'. Asterisks denote mean values from 2 or 3 rats per time point. Where n = 3; mean ± SD values are shown. All other values are from 1 rat per time point. The key to the tissues is as follows: 1 olfactory tubercles, 2 entorhinal cortex, 3 hypothalamus, 4 thalamus, 5 prefrontal cortex, 6 striata, 7 somatosensory cortex, 8 hippocampus, 9 occipital cortex, 10 inferior colliculi, 11 superior colliculi, 12 pons with medulla and 13 cerebellum. Again, plasma data (17) are shown for comparison with blood data (18).

What is claimed is:

1. A compound of formula (I):

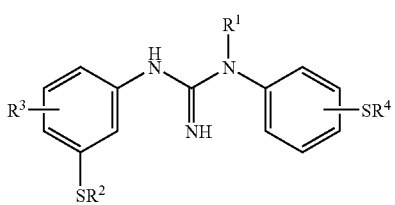

or a salt or solvate thereof, wherein:
R$^1$ is hydrogen or C$_{1-4}$ alkyl;
R$^2$ and R$^4$ are each independently selected from C$_{1-4}$ alkyl, [$^{11}$C]—C$_{1-4}$alkyl, and [$^{18}$F]—C$_{1-4}$ fluoroalkyl provided that at least one of R$^2$ and R$^4$ is [$^{11}$C]—C$_{1-4}$ alkyl or [$^{18}$F]—C$_{1-4}$ fluoroalkyl; and
R$^3$ is halo.

2. A compound according to claim 1 of formula (Ia):

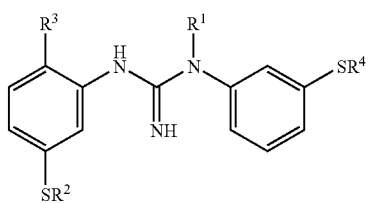

or a salt or solvate thereof, wherein R$^1$, R$^2$, R$^3$, and R$^4$ are as defined in claim 1.

3. A compound according to claim 1 selected from:
N-(2-chloro-5-[$^{18}$F]fluoromethylthio)-phenyl-N'-(3-methylthio)-phenyl-N'-methylguanidine;
N-(2-chloro-5-(2-[$^{18}$F]fluoroethylthio))-phenyl-N'-(3-methylthio)-phenyl-N'-methylguanidine;
N-(2-chloro-5-methylthio)-phenyl-N'-(3-[$^{18}$F]fluoromethylthio)-phenyl-N'-methylguanidine;
N-(2-chloro-5-methylthio)-phenyl-N'-(3-(2-[$^{18}$F]fluoroethylthio))-phenyl-N'-methylguanidine;
N-(2-chloro-5-[$^{11}$C]methylthio)-phenyl-N'-(3-methylthio)-phenyl-N'-methylguanidine;
N-(2-chloro-5-methylthio)-phenyl-N'-(3-[$^{11}$C]methylthio)-phenyl-N'-methylguanidine;
N-(2-chloro-5-[$^{11}$C]ethylthio)-phenyl-N'-(3-methylthio)-phenyl-N'-methylguanidine; and
N-(2-chloro-5-methylthio)-phenyl-N'-(3-[$^{11}$C]ethylthio)-phenyl-N'-methylguanidine or a salt or solvate of any thereof.

4. A radiopharmaceutical formulation comprising the compound according to claim 1 and a pharmaceutically acceptable excipient.

5. A method for the in vivo diagnosis or imaging of NMDA- mediated disease in a subject comprising administering a compound according to claim 1 and performing positron emission tomography.

* * * * *